United States Patent
Patil et al.

(10) Patent No.: US 9,822,323 B2
(45) Date of Patent: *Nov. 21, 2017

(54) LOW VISCOSITY LOW VOLATILITY LUBRICATING OIL BASE STOCKS AND PROCESSES FOR PREPARING SAME

(71) Applicant: ExxonMobil Research and Engineering Company, Annandale, NJ (US)

(72) Inventors: Abhimanyu O. Patil, Westfield, NJ (US); Satish Bodige, Wayne, NJ (US); Shuji Luo, Basking Ridge, NJ (US); Shane Deighton, Roselle Park, NJ (US); Halou Oumar-Mahamat, Belle Mead, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/297,292

(22) Filed: Oct. 19, 2016

(65) Prior Publication Data

US 2017/0137734 A1 May 18, 2017

Related U.S. Application Data

(60) Provisional application No. 62/254,746, filed on Nov. 13, 2015.

(51) Int. Cl.
*C10M 107/34* (2006.01)
*C07F 5/04* (2006.01)
(Continued)

(52) U.S. Cl.
CPC ......... *C10M 105/18* (2013.01); *C07C 43/202* (2013.01); *C07C 43/205* (2013.01);
(Continued)

(58) Field of Classification Search
CPC ................................................ C10M 2227/061
(Continued)

(56) References Cited

U.S. PATENT DOCUMENTS 3,036,003 A 5/1962 Verdol
3,172,892 A 3/1965 Le Suer et al.
(Continued)

FOREIGN PATENT DOCUMENTS

CA 2196852 A1 8/1997
EP 1040115 B1 6/2004
(Continued)

OTHER PUBLICATIONS

Cazorla, Clement et al., "O-Alkylation of phenol derivatives via a nucleophilic substitution", Green Chemistry, 2011, vol. 13, Issue 9, pp. 2482-2488.
(Continued)

*Primary Examiner* — Vishal Vasisth
(74) *Attorney, Agent, or Firm* — Robert A. Migliorini

(57) ABSTRACT

A composition that includes one or more compounds represented by the formula $$R_1-O-R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The composition has a viscosity ($Kv_{100}$) from about 1 to about 10 cSt at 100° C. as determined by ASTM D-445, a viscosity index (VI) from about −100 to about 300 as determined by ASTM D-2270, and a Noack volatility of no greater than 50 percent as determined by ASTM D-5800. The disclosure also relates to a process for producing the composition, a lubricating oil base stock and lubricating oil containing the composition, and a method of reducing boundary friction
(Continued)

| Base Stock# | Mol. Wt. | Kinematic Viscosity at 100°C (Kv100) | Kinematic Viscosity at 40°C (Kv40) | Viscosity Index (VI) | Noack Volatility (wt. %, TGA) |
|---|---|---|---|---|---|
| Example 1 | 333 | 2.43 | 10.1 | 36 | 21.5 |
| Example 2 | 347 | 2.89 | 13.3 | 40 | 17.3 |
| Example 3 | 256 | 2.36 | 12.9 | −166 | 43.1 |
| Example 4 | 282 | 2.34 | 7.99 | 108 | 21.4 |
| Example 5 | 310 | 2.77 | 10.0 | 122 | 10.8 |
| Example 6 | Blend of #4 & #5 | 2.54 | 8.94 | 115 | 17.0 |
| Example 7 | 296 | 2.41 | 9.33 | 65 | 23.2 |
| Example 8 | 312 | 3.19 | 19.5 | −62 | 16.2 |
| Example 9 | 285 | 2.82 | 15.8 | −63 | 25.7 |
| Example 10 | 256 | 2.29 | 11.3 | −72 | 49.8 | and improving dispersancy of polar additives of a lubricating oil by using as the lubricating oil a formulated oil containing the composition.

13 Claims, 3 Drawing Sheets

(51) Int. Cl.
    *C07C 43/00*     (2006.01)
    *C10M 105/18*     (2006.01)
    *C07C 43/20*     (2006.01)
    *C07C 43/205*     (2006.01)
    *C10M 105/72*     (2006.01)
    *C10M 105/66*     (2006.01)

(52) U.S. Cl.
    CPC ........ *C10M 105/66* (2013.01); *C10M 105/72* (2013.01); *C10M 2207/0406* (2013.01); *C10M 2215/0425* (2013.01); *C10M 2219/081* (2013.01); *C10N 2220/022* (2013.01); *C10N 2220/026* (2013.01); *C10N 2220/028* (2013.01); *C10N 2230/02* (2013.01); *C10N 2230/04* (2013.01); *C10N 2230/10* (2013.01); *C10N 2230/54* (2013.01); *C10N 2230/68* (2013.01); *C10N 2230/74* (2013.01); *C10N 2240/10* (2013.01)

(58) Field of Classification Search
    USPC .......................................................... 508/200
    See application file for complete search history.

(56) References Cited

U.S. PATENT DOCUMENTS

| | | | |
|---|---|---|---|
| 3,219,666 A | 11/1965 | Norman et al. | |
| 3,288,716 A | 11/1966 | Becraft et al. | |
| 3,316,177 A | 4/1967 | Dorer, Jr. | |
| 4,234,435 A | 11/1980 | Meinhardt et al. | |
| 4,292,195 A | 9/1981 | Morris | |
| 4,827,064 A | 5/1989 | Wu | |
| 4,827,073 A | 5/1989 | Wu | |
| 4,889,647 A | 12/1989 | Rowan et al. | |
| 4,892,680 A | 1/1990 | Ishida | |
| 4,956,122 A | 9/1990 | Watts et al. | |
| 4,978,464 A | 12/1990 | Coyle et al. | |
| 5,202,040 A | 4/1993 | Sanderson et al. | |
| 5,536,881 A | 7/1996 | Kawaguchi et al. | |
| 5,639,719 A | 6/1997 | Tanaka et al. | |
| 5,663,125 A | 9/1997 | Ishimaru et al. | |
| 5,705,458 A | 1/1998 | Roby et al. | |
| 5,994,277 A | 11/1999 | Ritchie et al. | |
| 6,406,642 B1 * | 6/2002 | Enna ...................... | C09K 5/045 252/67 |
| 6,423,746 B1 | 7/2002 | Yarbrough et al. | |
| 8,017,805 B2 | 9/2011 | Nalesnik | |
| 2006/0166844 A1 * | 7/2006 | Egawa ................. | C10M 105/18 508/579 |
| 2012/0045724 A1 | 2/2012 | Ohsawa et al. | |
| 2014/0080744 A1 | 3/2014 | Fujinami et al. | |
| 2015/0119307 A1 | 4/2015 | Patil et al. | |
| 2015/0337233 A1 | 11/2015 | Akao | |

FOREIGN PATENT DOCUMENTS

| | | | |
|---|---|---|---|
| JP | 2045596 A2 | 2/1990 | |
| JP | 4202397 A2 | 7/1992 | |
| JP | 6049473 A2 | 2/1994 | |
| JP | 6313180 A | 11/1994 | |
| JP | 7331271 A | 12/1995 | |
| JP | 8041482 A | 2/1996 | |
| JP | 9118890 A | 5/1997 | |
| JP | 3701558 B2 | 9/2005 | |
| SU | 1117296 A | 10/1984 | |
| WO | 99/31113 A1 | 6/1999 | |
| WO | 2009/134638 A2 | 11/2009 | |

OTHER PUBLICATIONS

Ashton, Peter R. et al., "Ru-Polypyridine Complexes Covalently Linked to Electron Acceptors as Wires for Light-Driven Pseudorotaxane-Type Molecular Machines", Chemistry—A European Journal, 1998, vol. 4, Issue 12, p. 2413.
Wolter, Martina et al., "Copper-Catalyzed Coupling of Aryl Iodides with Aliphatic Alcohols", Organic Letters, 2002, vol. 4, Issue 6, pp. 973-976.
The International Search Report and Written Opinion of PCT/US2016/057596 dated Dec. 23, 2016.
Lin, Whei Oh et al., "Short Chain Acyclic Crown Ethers", Monatshefte fur Chemie, 1980, vol. 112, No. 2, pp. 253-258.
"Konstitution and physikalische Eigenschaften von Athern, 7. Mitt.: Unterschiedlich substituierte Glykol-und Pentaerythritather", 1962, XP055328990.
Zamanian, Sara et al., "Catalytic Olefin Hydroalkoxylation by Nano Particles of Pollucite", Australian Journal of Chemistry, 2015, vol. 68, No. 6, pp. 981-986.
Van Duzee, Edward M. et al., "Hydrogenation and Hydrogenolysis of Ethers", Journal of the American Chemical Society, 1935, pp. 147-151.
PubChem, "SCHEMBL7923425", 2012, URL:https://pubchem.ncbi.nlm.nih.gov/compound/70229931#section=Top.
The International Search Report and Written Opinion of PCT/US2016/057593 dated Jan. 5, 2017.
PubChem, "SCHEMBL762240", 2007, URL:https://pubchem.ncbi.nim.nih.gov/compound/23522632#section=Top.
Cazorla, Clement et al., "O-Alkylation of phenol derivatives via a nucleophilic substitution", Green Chemistry, 2011, vol. 13, No. 9.
Murai, Masahito et al., "Bismuth (III)-Cataiyzed Dehydrative Etherification and Thioetherification of Phenolic Hydroxy Groups", Organic Letters, 2014, vol. 16, No. 14, pp. 3828-3831.
PubChem, "CHEMBL2271805", 2007, URL:https://pubchem.ncbi.nlm.nih=gov/compiound/14353132#section=Related-Coumpounds.
Rao, Maddali L.N. et al., "Pd-catalyzed chemoselective threefold cross-coupling of triarylbismuths with benzylic bromides", RSC Advances, 2013, vol. 3, No. 19.

* cited by examiner

Fig. 1

| Base Stock# | Mol. Wt. | Kinematic Viscosity at 100°C (Kv100) | Kinematic Viscosity at 40°C (Kv40) | Viscosity Index (VI) | Noack Volatility (wt. %, TGA) |
|---|---|---|---|---|---|
| Example 1 | 333 | 2.43 | 10.1 | 36 | 21.5 |
| Example 2 | 347 | 2.89 | 13.3 | 40 | 17.3 |
| Example 3 | 256 | 2.36 | 12.9 | -166 | 43.1 |
| Example 4 | 282 | 2.34 | 7.99 | 108 | 21.4 |
| Example 5 | 310 | 2.77 | 10.0 | 122 | 10.8 |
| Example 6 | Blend of #4 & #5 | 2.54 | 8.94 | 115 | 17.0 |
| Example 7 | 296 | 2.41 | 9.33 | 65 | 23.2 |
| Example 8 | 312 | 3.19 | 19.5 | -62 | 16.2 |
| Example 9 | 285 | 2.82 | 15.8 | -63 | 25.7 |
| Example 10 | 256 | 2.29 | 11.3 | -72 | 49.8 |

LOW VISCOSITY LOW VOLATILITY LUBRICATING OIL BASE STOCKS AND PROCESSES FOR PREPARING SAME

CROSS-REFERENCE TO RELATED APPLICATIONS

This application claims priority to U.S. Provisional Application Ser. No. 62/254,746 filed Nov. 13, 2015, which is herein incorporated by reference in its entirety. This application is related to one other co-pending U.S. application, filed on even date herewith, and identified by the following Ser. No. 15/297,333 entitled "Low Viscosity Low Volatility Lubricating Oil Base Stocks And Processes For Preparing Same." This co-pending U.S. application is hereby incorporated by reference herein in its entirety.

FIELD

This disclosure relates to low viscosity, low volatility compositions that include one or more alkyl substituted aryl ethers, a process for producing the compositions, a lubricating oil base stock and lubricating oil containing the composition, and a method of reducing boundary friction and improving dispersancy of polar additives of a lubricating oil by using as the lubricating oil a formulated oil containing the composition.

BACKGROUND

Lubricants in commercial use today are prepared from a variety of natural and synthetic base stocks admixed with various additive packages and solvents depending upon their intended application. The base stocks typically include mineral oils, polyalphaolefins (PAO), gas-to-liquid base oils (GTL), silicone oils, phosphate esters, diesters, polyol esters, and the like.

A major trend for passenger car engine oils (PCEOs) is an overall improvement in quality as higher quality base stocks become more readily available. Typically the highest quality PCEO products are formulated with base stocks such as PAOs or GTL stocks admixed with various additive packages.

For improving fuel economy, base oil viscosity is very important. Substantial improved fuel economy (>2%) requires breakthrough in: (1) base oil volatility (2) durability and (3) friction. Friction losses occur between the moving components within the engine. Models developed to date indicate that fuel economy is heavily influenced by the lubricant properties at high shear. The base stock contributes a greater proportion of the total viscosity under high shear conditions than under low shear. Lowering base stock viscosity is likely to have the largest impact on future fuel economy gains.

Current commercial PAO fluids (e.g., SpectraSyn™ 2) based on hydrocarbon and commercial esters (e.g., 2-ethylhexyl adipate, di-2-ethylhexyl azelate, Esterex™ A32, Esterex™ A34) do not adequately allow formulation of ultra-low viscosity lubricant while still meeting API specification (e.g., Noack volatility of 15% or less). In order to formulate ultra-low viscosity lubricant for fuel economy benefit, it is desirable to have low viscosity and low volatility properties co-exist in the same base stock, for meeting volatility requirement. In addition, the base stock should also possess adequate thermal and oxidative stability at high temperature to prevent or minimize deposit formation. Good compatibility with additives commonly used in lubricant formulations (PVL, CVL, industrial lubricants), good low temperature properties, and acceptable viscosity indices are also necessary for the base stocks.

Poly-α-olefins (PAOs) are important lube base stocks with many excellent lubricant properties, including high viscosity index (VI), low volatility and are available in various viscosity range ($Kv_{100}$ 2-300 cSt). However, PAOs are paraffinic hydrocarbons with low polarity. This low polarity leads to low solubility and dispersancy for polar additives or sludge generated during service. To compensate for this low polarity, lube formulators usually add one or multiple polar cobase stocks. Ester or alkylated naphthalene (AN) is usually present at 1 wt. % to 50 wt. % levels in many finished lubricant formulations to increase the fluid polarity which improves the solubility of polar additives and sludge.

Therefore, there is a need for polar cobase fluids that provide appropriate solubility and dispersibility for polar additives or sludge generated during service of lubricating oils.

Future automotive and industrial trend suggest that there will be a need for advanced additive technology and synthetic base stocks with substantially better thermal and oxidative stability. This is primarily because of smaller sump sizes that will have more thermal and oxidative stresses on the lubricants. Performance requirements have become more stringent in the past 10 to 20 years and the demand for longer drain intervals has grown steadily. Also, the use of Group II, III and IV base oils is becoming more widespread. Such base oils have very little sulfur content since natural sulfur-containing antioxidants are either absent or removed during the severe refining process.

It is known that lubricant oils used in internal combustion engines and transmission of automobile engines or trucks are subjected to demanding environments during use. These environments result in the lubricant suffering oxidation catalyzed by the presence of impurities in the oil, such as iron (wear) compounds and elevated temperatures. The oxidation manifests itself by increase in acid or viscosity and deposit formation or any combination of these symptoms. These are controlled to some extent by the use of antioxidants which can extend the useful life of the lubricating oil, particularly by reducing or preventing unacceptable viscosity increases. Besides oxidation inhibition, other parameters such as rust and wear control are also important.

A major challenge in engine oil formulation is simultaneously achieving improved fuel economy while also achieving appropriate solubility and dispersibility for polar additives or sludge generated during service of lubricating oils and oxidative stability.

Therefore, there is need for better additive and base stock technology for lubricant compositions that will meet ever more stringent requirements of lubricant users. In particular, there is a need for advanced additive technology and synthetic base stocks with improved fuel economy, solubility and dispersibility for polar additives or sludge generated during service of lubricating oils, and oxidative stability.

The present disclosure also provides many additional advantages, which shall become apparent as described below.

SUMMARY

This disclosure provides compositions that include one or more alkyl substituted aryl ethers (e.g., diphenylmethane ethers) that have desirable low viscosity/low volatility properties while exhibiting good high-temperature thermal-oxidative stability. Thus, the compositions of this disclosure provide a solution to achieve enhanced fuel economy and energy efficiency. In addition, good solvency for commonly used polar additives and potentially good hydrolytic and oxidative stability are other advantages of these compounds in base stock applications.

This disclosure relates in part to a composition comprising one or more compounds represented by the formula $$R_1\text{—}O\text{—}R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The composition has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800.

This disclosure also relates in part to a composition comprising one or more alkyl substituted aryl ethers represented by the formula $$R_1\text{—}O\text{—}R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The composition has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800. The one or more alkyl substituted aryl ethers are produced by a process comprising reacting a substituted or unsubstituted aryl alcohol with a substituted or unsubstituted alkyl halide, optionally in the presence of a catalyst, under reaction conditions sufficient to produce said one or more alkyl substituted aryl ethers.

This disclosure further relates in part to a composition comprising one or more alkyl substituted aryl ethers represented by the formula $$R_1\text{—}O\text{—}R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The composition has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800. The one or more alkyl substituted aryl ethers are produced by a process comprising reacting a substituted or unsubstituted aryl halide with a substituted or unsubstituted alkyl alcohol, optionally in the presence of a catalyst, under reaction conditions sufficient to produce said one or more alkyl substituted aryl ethers.

This disclosure yet further relates in part to a lubricating oil base stock comprising one or more compounds represented by the formula $$R_1\text{—}O\text{—}R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The lubricating oil base stock has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800.

This disclosure also relates in part to a lubricating oil comprising a lubricating oil base stock as a major component, and an alkyl substituted aryl ether cobase stock as a minor component. The alkyl substituted aryl ether cobase stock comprises one or more compounds represented by the formula $$R_1\text{—}O\text{—}R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The lubricating oil has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800.

This disclosure further relates in part to a method of reducing boundary friction and dispersancy of polar additives of a lubricating oil by using as the lubricating oil a formulated oil comprising a lubricating oil base stock as a major component, and alkyl substituted aryl ether cobase stock as a minor component. The alkyl substituted aryl ether cobase stock comprises one or more compounds represented by the formula $$R_1\text{—}O\text{—}R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The lubricating oil has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800.

It has been surprisingly found that outstanding low viscosity low volatility properties, good high-temperature thermal and oxidative stability, good solvency for polar additives, and traction benefits (e.g., reduced boundary friction), can be attained in an engine lubricated with a lubricating oil by using as the lubricating oil a formulated oil in accordance with this disclosure. In particular, a lubricating oil base stock comprising one or more alkyl substituted aryl ethers (e.g., diphenylmethane ethers) exhibits low viscosity, low volatility, desired solvency for polar additives, and superior oxidative stability, which helps to prolong the useful life of lubricants and significantly improve the durability and resistance of lubricants when exposed to high temperatures. The lubricating oils of this disclosure are particularly advantageous as passenger vehicle engine oil (PVEO) products.

Further objects, features and advantages of the present disclosure will be understood by reference to the following drawings and detailed description.

BRIEF DESCRIPTION OF THE DRAWINGS

FIG. 1 shows kinematic viscosities, viscosity indices (VI) and volatility of selected Group V base stocks in accordance with Example 11.

DETAILED DESCRIPTION

Figure 2:
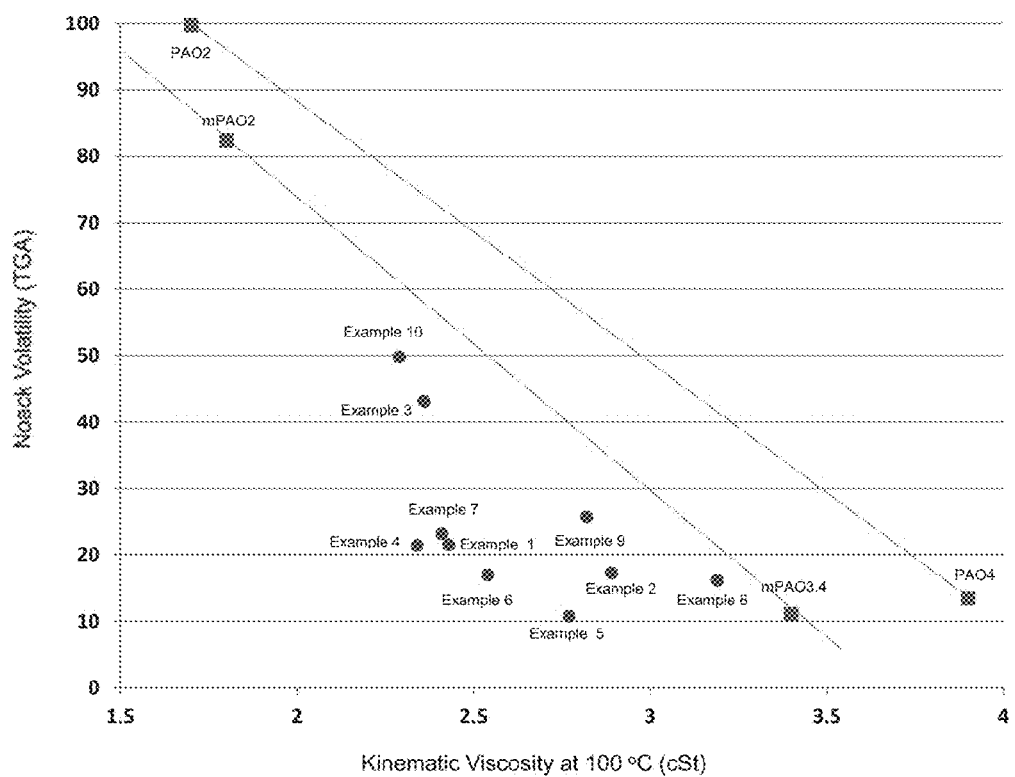
FIG. 2 graphically shows kinematic viscosity at 100° C. (x-axis) and TGA Noack (y-axis) of PAO4, mPAO3.4, PAO2, mPAO2 and synthetic fluids of Examples 1-10 in accordance with Example 11.

All numerical values within the detailed description and the claims herein are modified by "about" or "approximately" the indicated value, and take into account experimental error and variations that would be expected by a person having ordinary skill in the art.

The compositions of this disclosure contain an aryl group and ether functionality. These compositions exhibit (1) outstanding low viscosity low volatility properties, (2) good high-temperature thermal and oxidative stability, (3) good solvency for polar additives, and (4) traction benefits, which make them attractive as Group V synthetic base stocks in high performance, fuel economy lubricant applications.

Low viscosity base stocks (e.g., kinematic viscosity at 100° C., 2-3 cSt) currently available in the marketplace are too volatile (Noack>15-20%) to be used for formulating next-generation ultra-low viscosity engine oils (i.e., xxW-4→xxW-16). These base stocks (e.g., SpectraSyn™ 2, GTL3, bis(2-ethylhexyl) adipate, di-2-ethylhexyl azelate, Esterex™ A32) are unable to provide formulated engine oils that also meet current volatility API specification. In addition, current Group V ester base stocks generally have poor high temperature oxidation stability which can cause operational problems in engine, potentially causing high deposit formation. The present disclosure identifies aryl ethers that have desirable low viscosity and low volatility properties while exhibiting traction benefits, good deposit control behavior and good high-temperature thermal-oxidative stability, hence provides a solution to achieve enhanced fuel economy and energy efficiency. In addition, good solvency for commonly used polar additives and potentially good hydrolytic stability are other advantages of these compounds in base stock applications.

In accordance with this disclosure, an alkyl ether chain is attached to an aryl group (e.g., naphthalene, benzene, diphenylmethane, and the like) to obtain Group V fluids. By changing the alkyl portion, molecules with varying polarity (and hydrocarbon compatibility) can be synthesized. Traditional Group V fluids, such as alkylated naphthalene (AN), are prepared via acid catalyst alkylation reaction that tends to give mixed alkylated products. The fluids of this disclosure are precise molecules. These molecules can be used as base stocks or as cobase stocks along with mPAO (metallocene catalyst based poly-alpha-olefins), PAO, Group I-III+, GTL, ionic liquids, and the like.

As indicated above, alkyl substituted aryl ether base stock and cobase stock components useful in this disclosure include, for example, compositions containing one or more compounds represented by the formula $$R_1—O—R_2$$

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The composition has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800.

Preferred alkyl substituted aryl ether base stock and cobase stock components include those in which $R_1$ is substituted or unsubstituted phenyl, benzyl, naphthyl, or diphenyl (e.g., diphenylmethane), and $R_2$ is substituted or unsubstituted, linear or branched alkyl ($C_4$-$C_{40}$).

Other preferred alkyl substituted aryl ether base stock and cobase stock components include alkyl ($C_4$-$C_{40}$) substituted aryl ethers, and the like.

Preferred alkyl substituted aryl ether base stock and cobase stock components have a viscosity ($Kv_{100}$) from about 1 to about 8, more preferably from about 2 to about 6, at 100° C. as determined by ASTM D-445, a viscosity index (VI) from about −100 to about 300, more preferably from about 0 to about 150, even more preferably from about 25 to about 100, as determined by ASTM D-2270, and a Noack volatility of no greater than 75 percent, more preferably no greater than 50 percent, even more preferably no greater than 25 percent, as determined by ASTM D-5800.

Illustrative alkyl substituted aryl ether base stock and cobase stock components useful in the present disclosure comprise one or more compounds represented by the formulae

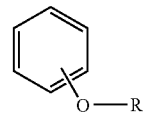

wherein R is a substituted or unsubstituted, linear or branched, alkyl group having from about 4 to about 40 carbon atoms;

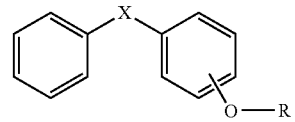

wherein R is a substituted or unsubstituted, linear or branched, alkyl group having from about 4 to about 40 carbon atoms, and X is $CH_2$, O, NR' or S, wherein R' is hydrogen or an alkyl group having from 1 to about 4 carbon atoms; and

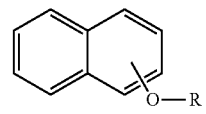

wherein R is a substituted or unsubstituted, linear or branched, alkyl group having from about 4 to about 40 carbon atoms.

Illustrative alkyl substituted aryl ether base stock and cobase stock components useful in the present disclosure include, for example, 1-(2-hexyldecyloxy)-4-methylbenzene, 4-(2-hexyldecyloxy)-1,2-dimethylbenzene, 2-(2-ethylhexyloxy)naphthalene, 3-heptyloxy-2,6-diphenylmethane, 3-nonyloxy-2,6-diphenylmethane, 3-(2-ethylhexyloxy)-2,6-diphenylmethane, 1-(2-butyloctyloxy)naphthalene, 2-(3,7-dimethyloctyloxy)naphthalene, 2-(2-ethylhexyloxy)naphthalene, and the like.

Illustrative alkyl substituted aryl ether base stock and cobase stock components useful in the present disclosure include, for example, the product of reacting a substituted or unsubstituted aryl alcohol with a substituted or unsubstituted alkyl halide, optionally in the presence of a catalyst, under reaction conditions sufficient to produce said one or more alkyl substituted aryl ethers. Similarly one or more alkyl substituted aryl ethers can be produced by reacting a substituted or unsubstituted aryl halide with a substituted or unsubstituted alkyl alcohol, optionally in the presence of a catalyst, under reaction conditions sufficient to produce the one or more alkyl substituted aryl ethers.

Illustrative aryl alcohols useful in the process of this disclosure include, for example, 4-benzylphenol, 5,6,7,8,-tetrahydro-1-napthol, 5,6,7,8,-tetrahydro-2-napthol, 2-napthol, 1-napthol, 2-benzylphenol, 4-phenoxyphenol, 2-methyl-1-napthol, 6-methoxy-2-napthol, 3-methoxy-2-napthol, 7-methoxy-2-napthol, 3-phenylphenol, 2-phenylphenol, 4-phenylphenol, and the like.

Illustrative alkyl halides useful in the process of this disclosure include, for example, 1-bromoheptane, 1-bromononane, 2-ethylhexyl bromide, 2-bromopentane, 1-bromooctane, 2-bromooctane, 1-bromononane, 2-bromononane, 1-bromo-3,-7-dimethyloctane, 2-bromodecane, 1-bromododecane, 2-bromododecane, 1-bromoheptane, 2-bromoheptane, 1-bromodecane, 1-bromoundecane, 2-bromoundecane, 1-bromotridecane, 1-bromopentadecane, 1-bromohexadecane, 1-bromoheptadecane, 1-bromooctadecane, 1-bromononadecane, 1-bromoeicosane and the like.

Reaction conditions for the reaction of the aryl alcohol with the alkyl halide, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to about 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 48 hours, preferably from about 1 to 36 hours, and more preferably from about 2 to 24 hours.

Other illustrative alkyl substituted aryl ether base stock and cobase stock components useful in the present disclosure include, for example, the product of reacting a substituted or unsubstituted aryl halide with a substituted or unsubstituted alkyl alcohol, optionally in the presence of a catalyst, under reaction conditions sufficient to produce said one or more alkyl substituted aryl ethers.

Illustrative aryl halides useful in the process of this disclosure include, for example, 1-iodo-4-methylbenzene, 1-iodo-2,4-dimethylbenzene, 2-iodonaphthalene, 3-bromodiphenylamine, 2-iodotoluene, 3-iodotoluene, 1-bromo-2, 3,-dimethylbenzene, 1-bromo-2.4,-dimethylbenzene, 1-bromo-2-ethylbenzene, 1-bromo-4-ethylbenzene, 2-bromo-1,3-dimethylbenzene, 2-bromo-1, 4-dimethylbenzene, 2-bromo-1,2 dimethylbenzene, 1-bromo-2-ethoxybenzene, 1-iodo-3,4-dimethylbenzene, 1-iodo-3,5-dimethylbenzene, 2-iodo-1, 3-dimethylbenzene, 7-bromo-1H-indene, 1-bromo-3-isopropylbenzene, 1-bromo-4-isopropylbenzene, 1-iodo-4-isopropylbenzene, 2-iodocumene, 5-iodo-1, 2,3,-trimethylbenzene, 1-bromo-3-(trimethylsiliyl)benzene, 1-bromo-4-(trimethylsiliyl)benzene, 2-bromonapthalene, 2-iodonapthalene, 1-bromo-4-tert, butylbenzene, 1-iodo-4-tertbutylbenzene, 1-bromo-4-methylnapthalene, 1-bromo-2-methylnapthalene, 2-bromobiphenyl, 4-bromobiphenyl, 3-bromobiphenyl, 3-bromophenathrene, 2-bromofluorene, 9-bromofluorene, 9-bromoanthracene, 9-bromophenathrene, 9-iodophenathrene, 1-bromo-3,5-tert-butylbenzene, 1-bromopyrene, and the like.

Illustrative alkyl alcohols useful in the process of this disclosure include, for example, 2-hexyldecane-1-ol, 2-ethylhexane-1-ol, 1-heptanol, 2-heptanol, 2,2-dimethyl-3-pentanol, 2,3-dimethyl-1-pentanol, 2-methyl-1-hexanol, 2-methyl-3-hexanol, 2-ethyl-3-pentanol, 5-methyl-2-pentanol, 2,4,4-trimethyl-1-pentanol, 2-propyl-1-pentanol, 2-octanol, 4-octanol, 6-methyl-2-heptanol, 6-methyl-3, 2,6-dimethyl-4-heptanol, 2-nonanol, 2-decanol, 1-decanol, 3,7-dimethyl-1-octanol, 3,7-dimethyl-3-octanol, 1-undecanol, 2-undecanol, 2-butyl-1-octanol, 2-dodecanol, 1-tridecanol, 1-tetradecanol, 2-tetradecanol, 1-hexadecanol, 2-hexadecanol, 2-hexyl-1-decanol, 1-heptadecanol, 2-octal-1-dodecanol, and the like.

Reaction conditions for the reaction of the aryl halide with the alkyl alcohol, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to about 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 48 hours, preferably from about 1 to 36 hours, and more preferably from about 2 to 24 hours.

Examples of techniques that can be employed to characterize the compositions formed by the process described above include, but are not limited to, analytical gas chromatography, nuclear magnetic resonance, thermogravimetric analysis (TGA), inductively coupled plasma mass spectrometry, differential scanning calorimetry (DSC), volatility and viscosity measurements.

This disclosure provides lubricating oils useful as engine oils and in other applications characterized by excellent oxidative stability. The lubricating oils are based on high quality base stocks including a major portion of a hydrocarbon base fluid such as a PAO or GTL with a secondary cobase stock component which is an alkyl substituted aryl ether as described herein. The lubricating oil base stock can be any oil boiling in the lube oil boiling range, typically between about 100 to 450° C. In the present specification and claims, the terms base oil(s) and base stock(s) are used interchangeably.

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM method D 2270-93 [1998]. VI is related to kinematic viscosities measured at 40° C. and 100° C. using ASTM Method D 445-01.

Lubricating Oil Base Stocks

A wide range of lubricating oils is known in the art. Lubricating oils that are useful in the present disclosure are both natural oils and synthetic oils. Natural and synthetic oils (or mixtures thereof) can be used unrefined, refined, or rerefined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve the at least one lubricating oil property. One skilled in the art is familiar with many purification processes. These processes include solvent extraction, secondary distillation, acid extraction, base extraction, filtration, and percolation. Rerefined oils are obtained by processes analogous to refined oils but using an oil that has been previously used as a feed stock.

Groups I, II, III, IV and V are broad categories of base oil stocks developed and defined by the American Petroleum Institute (API Publication 1509; www.API.org) to create guidelines for lubricant base oils. Group I base stocks generally have a viscosity index of between about 80 to 120 and contain greater than about 0.03% sulfur and less than about 90% saturates. Group II base stocks generally have a viscosity index of between about 80 to 120, and contain less than or equal to about 0.03% sulfur and greater than or equal to about 90% saturates. Group III stock generally has a viscosity index greater than about 120 and contains less than or equal to about 0.03% sulfur and greater than about 90% saturates. Group IV includes polyalphaolefins (PAO). Group V base stocks include base stocks not included in Groups I-IV. The table below summarizes properties of each of these five groups.

| Base Oil Properties | | | |
| --- | --- | --- | --- |
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | Includes polyalphaolefins (PAO) products | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Group II and/or Group III hydroprocessed or hydrocracked base stocks, as well as synthetic oils such as polyalphaolefins, alkyl aromatics and synthetic esters, i.e. Group IV and Group V oils are also well known base stock oils.

Synthetic oils include hydrocarbon oil such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil base stocks, the Group IV API base stocks, are a commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073, which are incorporated herein by reference in their entirety. Group IV oils, that is, the PAO base stocks have viscosity indices preferably greater than 130, more preferably greater than 135, still more preferably greater than 140.

Esters in a minor amount may be useful in the lubricating oils of this disclosure. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols such as the neopentyl polyols: e.g., neopentyl glycol, trimethylol ethane, 2-methyl-2-propyl-1,3-propanediol, trimethylol propane, pentaerythritol and dipentaerythritol with alkanoic acids containing at least about 4 carbon atoms, preferably $C_5$ to $C_{30}$ acids such as saturated straight chain fatty acids including caprylic acid, capric acids, lauric acid, myristic acid, palmitic acid, stearic acid, arachic acid, and behenic acid, or the corresponding branched chain fatty acids or unsaturated fatty acids such as oleic acid, or mixtures of any of these materials.

Esters should be used in an amount such that the improved wear and corrosion resistance provided by the lubricating oils of this disclosure are not adversely affected.

Non-conventional or unconventional base stocks and/or base oils include one or a mixture of base stock(s) and/or base oil(s) derived from: (1) one or more Gas-to-Liquids (GTL) materials, as well as (2) hydrodewaxed, or hydroisomerized/cat (and/or solvent) dewaxed base stock(s) and/or base oils derived from synthetic wax, natural wax or waxy feeds, mineral and/or non-mineral oil waxy feed stocks such as gas oils, slack waxes (derived from the solvent dewaxing of natural oils, mineral oils or synthetic oils; e.g., Fischer-Tropsch feed stocks), natural waxes, and waxy stocks such as gas oils, waxy fuels hydrocracker bottoms, waxy raffinate, hydrocrackate, thermal crackates, foots oil or other mineral, mineral oil, or even non-petroleum oil derived waxy materials such as waxy materials recovered from coal liquefaction or shale oil, linear or branched hydrocarbyl compounds with carbon number of about 20 or greater, preferably about 30 or greater and mixtures of such base stocks and/or base oils.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL base stocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL base stock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce lube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL base stock(s) and/or base oil(s) derived from GTL materials, especially, hydrodewaxed or hydroisomerized/followed by cat and/or solvent dewaxed wax or waxy feed, preferably F-T material derived base stock(s) and/or base oil(s), are characterized typically as having kinematic viscosities at 100° C. of from about 2 mm$^2$/s to about 50 mm$^2$/s (ASTM D445). They are further characterized typically as having pour points of −5° C. to about −40° C. or lower (ASTM D97). They are also characterized typically as having viscosity indices of about 80 to about 140 or greater (ASTM D2270).

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this materially especially suitable for the formulation of low SAP products.

The term GTL base stock and/or base oil and/or wax isomerate base stock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL base stock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, Group V and Group VI oils and mixtures thereof, preferably API Group II, Group III, Group IV, Group V and Group VI oils and mixtures thereof, more preferably the Group III to Group VI base oils due to their exceptional volatility, stability, viscometric and cleanliness features. Minor quantities of Group I stock, such as the amount used to dilute additives for blending into formulated lube oil products, can be tolerated but should be kept to a minimum. i.e. amounts only associated with their use as diluent/carrier oil for additives used on an "as received" basis. Even in regard to the Group II stocks, it is preferred that the Group II stock be in the higher quality range associated with that stock, i.e. a Group II stock having a viscosity index in the range 100<VI<120.

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) and hydrodewaxed, or hydroisomerized/cat (and/or solvent) dewaxed base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

The base stock component of the present lubricating oils will typically be from 50 to 99 weight percent of the total composition (all proportions and percentages set out in this specification are by weight unless the contrary is stated) and more usually in the range of 80 to 99 weight percent.

Alkyl Substituted Aryl Ether Base Stock and Cobase Stock Components

Alkyl substituted aryl ether base stock and cobase stock components useful in this disclosure include, for example, compositions containing one or more compounds represented by the formula

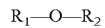

wherein $R_1$ is a substituted or unsubstituted aryl or polyaryl group having from about 4 to about 40 carbon atoms, and $R_2$ is a substituted or unsubstituted, linear or branched, alkyl group having from about 4 to about 40 carbon atoms. The composition has a viscosity ($Kv_{100}$) from about 1 to about 10 at 100° C. as determined by ASTM D-445, a viscosity index (VI) from about −100 to about 300 as determined by ASTM D-2270, and a Noack volatility of no greater than 50 percent as determined by ASTM D-5800.

Preferred alkyl substituted aryl ether base stock and cobase stock components include those in which $R_1$ is substituted or unsubstituted phenyl, benzyl, naphthyl, or diphenyl (e.g., diphenylmethane), and $R_2$ is substituted or unsubstituted, linear or branched, alkyl ($C_4$-$C_{40}$).

Other preferred alkyl substituted aryl ether base stock and cobase stock components include alkyl ($C_4$-$C_{40}$) substituted aryl ethers, and the like.

Preferred alkyl substituted aryl ether base stock and cobase stock components have a viscosity ($Kv_{100}$) from about 1 to about 8, preferably from about 2 to about 6, more preferably from about 2 to about 4, at 100° C. as determined by ASTM D-445, a viscosity index (VI) from about −200 to about 300, preferably from about 0 to about 150, even more preferably from about 25 to about 100 as determined by ASTM D-2270, and a Noack volatility of no greater than 75 percent, preferably no great than 50 percent, more preferably no greater than 25 percent, as determined by ASTM D-5800.

Preferred alkyl substituted aryl ether base stock and cobase stock components have a viscosity ($Kv_{100}$) from about 2 to about 8, more preferably from about 2 to about 6, at 100° C. as determined by ASTM D-445, a viscosity index (VI) from about 25 to about 125, more preferably from about 50 to about 100, as determined by ASTM D-2270, and a Noack volatility of no greater than 25 percent, more preferably no greater than 20 percent, as determined by ASTM D-5800.

Illustrative alkyl substituted aryl ether base stock and cobase stock components useful in the present disclosure comprise one or more compounds represented by the formulae

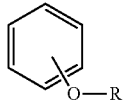

wherein R is a substituted or unsubstituted, linear or branched, alkyl group having from about 4 to about 40 carbon atoms;

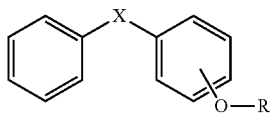

wherein R is a substituted or unsubstituted, linear or branched, alkyl group having from about 4 to about 40 carbon atoms, and X is $CH_2$, O, NR' or S, wherein R' is hydrogen or an alkyl group having from 1 to about 4 carbon atoms; and

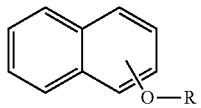

wherein R is a substituted or unsubstituted, linear or branched, alkyl group having from about 4 to about 40 carbon atoms.

Illustrative alkyl substituted aryl ether base stock and cobase stock components useful in the present disclosure include, for example, 1-(2-hexyldecyloxy)-4-methylbenzene, 4-(2-hexyldecyloxy)-1,2-dimethylbenzene, 2-(2-ethylhexyloxy)naphthalene, 3-heptyloxy-2,6-diphenylmethane, 3-nonyloxy-2,6-diphenylmethane, 3-(2-ethylhexyloxy)-2,6-diphenylmethane, 1-(2-butyloctyloxy)naphthalene, 2-(3,7-dimethyloctyloxy)naphthalene, 2-(2-ethylhexyloxy)naphthalene, and the like.

Illustrative alkyl substituted aryl ether base stock and cobase stock components useful in the present disclosure include, for example, the product of reacting a substituted or unsubstituted aryl alcohol with a substituted or unsubstituted alkyl halide, optionally in the presence of a catalyst, under reaction conditions sufficient to produce said one or more alkyl substituted aryl ethers.

Illustrative aryl alcohols useful in the process of this disclosure include, for example, 4-benzylphenol, 5,6,7,8,-tetrahydro-1-napthol, 5,6,7,8,-tetrahydro-2-napthol, 2-napthol, 1-napthol, 2-benzylphenol, 4-phenoxyphenol, 2-methyl-1-napthol, 6-methoxy-2-napthol, 3-methoxy-2-napthol, 7-methoxy-2-napthol, 3-phenylphenol, 2-phenylphenol, 4-phenylphenol, and the like.

Illustrative alkyl halides useful in the process of this disclosure include, for example, 1-bromoheptane, 1-bromononane, 2-ethylhexyl bromide, 2-bromopentane, 1-bromooctane, 2-bromooctane, 1-bromononane, 2-bromononane, 1-bromo-3,-7-dimethyloctane, 2-bromodecane, 1-bromododecane, 2-bromododecane, 1-bromoheptane, 2-bromoheptane, 1-bromodecane, 1-bromoundecane, 2-bromoundecane, 1-bromotridecane, 1-bromopentadecane, 1-bromohexadecane, 1-bromoheptadecane, 1-bromooctadecane, 1-bromononadecane, 1-bromoeicosane and the like.

Other illustrative alkyl substituted aryl ether base stock and cobase stock components useful in the present disclosure include, for example, the product of reacting a substituted or unsubstituted aryl halide with a substituted or unsubstituted alkyl alcohol, optionally in the presence of a catalyst, under reaction conditions sufficient to produce said one or more alkyl substituted aryl ethers.

Illustrative aryl halides useful in the process of this disclosure include, for example, 1-iodo-4-methylbenzene, 1-iodo-2,4-dimethylbenzene, 2-iodonaphthalene, 3-bromodiphenylamine, 2-iodotoluene, 3-iodotoluene, 1-bromo-2, 3,-dimethylbenzene, 1-bromo-2,4,-dimethylbenzene, 1-bromo-2-ethylbenzene, 1-bromo-4-ethylbenzene, 2-bromo-1,3-dimethylbenzene, 2-bromo-1, 4-dimethylbenzene, 2-bromo-1,2 dimethylbenzene, 1-bromo-2-ethoxybenzene, 1-iodo-3,4-dimethylbenzene, 1-iodo-3,5-dimethylbenzene, 2-iodo-1, 3-dimethylbenzene, 7-bromo-1H-indene, 1-bromo-3-isopropylbenzene, 1-bromo-4-isopropylbenzene, 1-iodo-4-isopropylbenzene, 2-iodocumene, 5-iodo-1, 2,3,-trimethylbenzene, 1-bromo-3-(trimethylsiliyl)benzene, 1-bromo-4-(trimethylsiliyl)benzene, 2-bromonapthalene, 2-iodonapthalene, 1-bromo-4-tert.butylbenzene, 1-iodo-4-tertbutylbenzene, 1-bromo-4-methylnapthalene, 1-bromo-2-methylnapthalene, 2-bromobiphenyl, 4-bromobiphenyl, 3-bromobiphenyl, 3-bromophenathrene, 2-bromofluorene, 9-bromofluorene, 9-bromoanthracene, 9-bromophenathrene, 9-iodophenathrene, 1-bromo-3,5-tert-butylbenzene, 1-bromopyrene, and the like.

Illustrative alkyl alcohols useful in the process of this disclosure include, for example, 2-hexyldecane-1-ol, 2-ethylhexane-1-ol, 1-heptanol, 2-heptanol, 2,2-dimethyl-3-pentanol, 2,3-dimethyl-1-pentanol, 2-methyl-1-hexanol, 2-methyl-3-hexanol, 2-ethyl-3-pentanol, 5-methyl-2-pentanol, 2,4,4-trimethyl-1-pentanol, 2-propyl-1-pentanol, 2-octanol, 4-octanol, 6-methyl-2-heptanol, 6-methyl-3, 2,6-dimethyl-4-heptanol, 2-nonanol, 2-decanol, 1-decanol, 3,7-dimethyl-1-octanol, 3,7-dimethyl-3-octanol, 1-undecanol, 2-undecanol, 2-butyl-1-octanol, 2-dodecanol, 1-tridecanol, 1-tetradecanol, 2-tetradecanol, 1-hexadecanol, 2-hexadecanol, 2-hexyl-1-decanol, 1-heptadecanol, 2-octal-1-dodecanol, and the like.

The alkyl substituted aryl ether cobase stock component is preferably present in an amount sufficient for providing oxidative stability in the lubricating oil. The alkyl substituted aryl ether cobase stock component is present in the lubricating oils of this disclosure in an amount from about 1 to about 50 weight percent, preferably from about 5 to about 30 weight percent, and more preferably from about 10 to about 20 weight percent.

The alkyl substituted aryl ether base stock component of the present lubricating oils will typically be from 20 to 80 weight percent or from 50 to 99 weight percent of the total composition (all proportions and percentages set out in this specification are by weight unless the contrary is stated) and more usually in the range of 80 to 99 weight percent.

Other Additives

The formulated lubricating oil useful in the present disclosure may additionally contain one or more of the other commonly used lubricating oil performance additives including but not limited to dispersants, other detergents, corrosion inhibitors, rust inhibitors, metal deactivators, other anti-wear agents and/or extreme pressure additives, anti-seizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

The types and quantities of performance additives used in combination with the instant disclosure in lubricant compositions are not limited by the examples shown herein as illustrations.

Viscosity Improvers

Viscosity improvers (also known as Viscosity Index modifiers, and VI improvers) increase the viscosity of the oil composition at elevated temperatures which increases film thickness, while having limited effect on viscosity at low temperatures.

Suitable viscosity improvers include high molecular weight hydrocarbons, polyesters and viscosity index improver dispersants that function as both a viscosity index improver and a dispersant. Typical molecular weights of these polymers are between about 10,000 to 1,000,000, more typically about 20,000 to 500,000, and even more typically between about 50,000 and 200,000.

Examples of suitable viscosity improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The amount of viscosity modifier may range from zero to 8 wt %, preferably zero to 4 wt %, more preferably zero to 2 wt % based on active ingredient and depending on the specific viscosity modifier used.

Antioxidants

Typical anti-oxidant include phenolic anti-oxidants, aminic anti-oxidants and oil-soluble copper complexes.

The phenolic antioxidants include sulfurized and non-sulfurized phenolic antioxidants. The terms "phenolic type" or "phenolic antioxidant" used herein includes compounds having one or more than one hydroxyl group bound to an aromatic ring which may itself be mononuclear, e.g., benzyl, or poly-nuclear, e.g., naphthyl and spiro aromatic compounds. Thus "phenol type" includes phenol per se, catechol, resorcinol, hydroquinone, naphthol, etc., as well as alkyl or alkenyl and sulfurized alkyl or alkenyl derivatives thereof, and bisphenol type compounds including such biphenol compounds linked by alkylene bridges sulfuric bridges or oxygen bridges. Alkyl phenols include mono- and poly-alkyl or alkenyl phenols, the alkyl or alkenyl group containing from about 3-100 carbons, preferably 4 to 50 carbons and sulfurized derivatives thereof, the number of alkyl or alkenyl groups present in the aromatic ring ranging from 1 to up to the available unsatisfied valences of the aromatic ring remaining after counting the number of hydroxyl groups bound to the aromatic ring.

Generally, therefore, the phenolic anti-oxidant may be represented by the general formula:

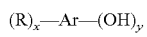

where Ar is selected from the group consisting of:

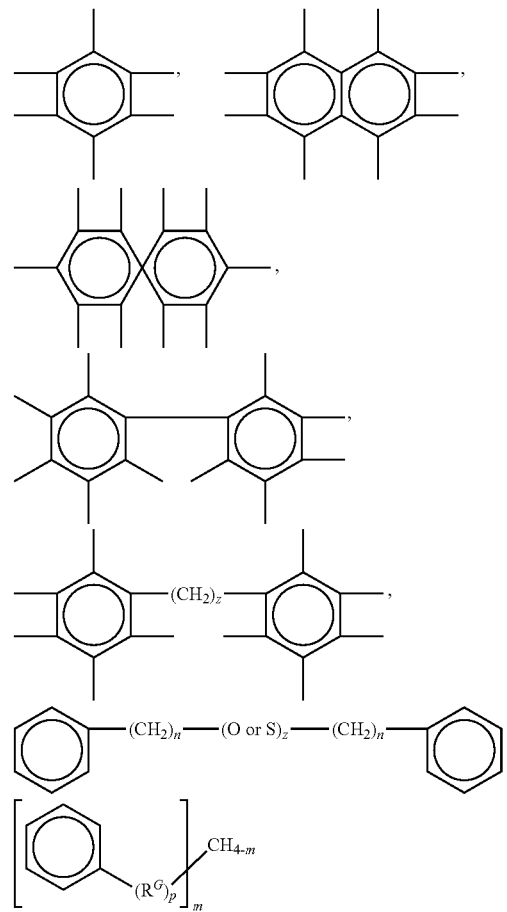

wherein R is a $C_3$-$C_{100}$ alkyl or alkenyl group, a sulfur substituted alkyl or alkenyl group, preferably a $C_4$-$C_{50}$ alkyl or alkenyl group or sulfur substituted alkyl or alkenyl group, more preferably $C_3$-$C_{100}$ alkyl or sulfur substituted alkyl group, most preferably a $C_4$-$C_{10}$ alkyl group, $R^G$ is a $C_1$-$C_{100}$ alkylene or sulfur substituted alkylene group, preferably a $C_2$-$C_{50}$ alkylene or sulfur substituted alkylene group, more preferably a $C_2$—$C_2$ alkylene or sulfur substituted alkylene group, y is at least 1 to up to the available valences of Ar, x ranges from 0 to up to the available valances of Ar-y, z ranges from 1 to 10, n ranges from 0 to 20, and m is 0 to 4 and p is 0 or 1, preferably y ranges from 1 to 3, x ranges from 0 to 3, z ranges from 1 to 4 and n ranges from 0 to 5, and p is 0.

Preferred phenolic anti-oxidant compounds are the hindered phenolics and phenolic esters which contain a sterically hindered hydroxyl group, and these include those derivatives of dihydroxy aryl compounds in which the hydroxyl groups are in the o- or p-position to each other. Typical phenolic anti-oxidants include the hindered phenols substituted with $C_1+$ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; 2-methyl-6-t-butyl-4-dodecyl phenol; 2,6-di-t-butyl-4 methyl phenol; 2,6-di-t-butyl-4-ethyl phenol; and 2,6-di-t-butyl 4 alkoxy phenol; and

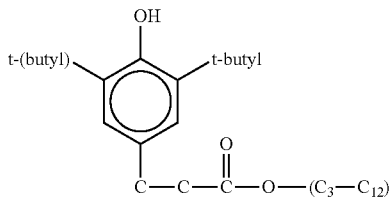

Phenolic type anti-oxidants are well known in the lubricating industry and commercial examples such as Ethanox® 4710, Irganox-1076. Irganox® L1035, Irganox®® 1010, Irganox® L109, Irganox® L118, Irganox® L135 and the like are familiar to those skilled in the art. The above is presented only by way of exemplification, not limitation on the type of phenolic anti-oxidants which can be used.

The phenolic anti-oxidant can be employed in an amount in the range of about 0.1 to 3 wt %, preferably about 1 to 3 wt %/o, more preferably 1.5 to 3 wt %/o on an active ingredient basis.

Aromatic amine anti-oxidants include phenyl-α-naphthyl amine which is described by the following molecular structure:

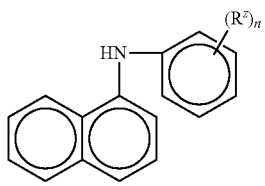

wherein $R^z$ is hydrogen or a $C_1$ to $C_{14}$ linear or $C_3$ to $C_{14}$ branched alkyl group, preferably $C_1$ to $C_{10}$ linear or $C_3$ to $C_{10}$ branched alkyl group, more preferably linear or branched $C_6$ to $C_8$ and n is an integer ranging from 1 to 5 preferably 1. A particular example is Irganox L06.

Other aromatic amine anti-oxidants include other alkylated and non-alkylated aromatic amines such as aromatic monoamines of the formula $R^8R^9R^{10}N$ where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$ where $R^{ii}$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to about 20 carbon atoms, and preferably contains from about 6 to 12 carbon atoms. The aliphatic group is a saturated aliphatic group. Preferably, both Re and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines anti-oxidants have alkyl substituent groups of at least about 6 carbon atoms. Examples of aliphatic groups include hexyl, heptyl, octyl, nonyl, and decyl. Generally, the aliphatic groups will not contain more than about 14 carbon atoms. The general types of such other additional amine anti-oxidants which may be present include diphenylamines, phenothiazines, imidodibenzyls and diphenyl phenylene diamines. Mixtures of two or more of such other additional aromatic amines may also be present. Polymeric amine antioxidants can also be used.

Another class of anti-oxidant used in lubricating oil compositions and which may also be present are oil-soluble copper compounds. Any oil-soluble suitable copper compound may be blended into the lubricating oil. Examples of suitable copper antioxidants include copper dihydrocarbyl thio- or dithio-phosphates and copper salts of carboxylic acid (naturally occurring or synthetic). Other suitable copper salts include copper dithiacarbamates, sulphonates, phenates, and acetylacetonates. Basic, neutral, or acidic copper Cu(I) and or Cu(II) salts derived from alkenyl succinic acids or anhydrides are known to be particularly useful.

Such antioxidants may be used individually or as mixtures of one or more types of antioxidants, the total amount employed being an amount of about 0.50 to 5 wt %, preferably about 0.75 to 3 wt % (on an as-received basis).

Detergents

In addition to the alkali or alkaline earth metal salicylate detergent which is an essential component in the present disclosure, other detergents may also be present. While such other detergents can be present, it is preferred that the amount employed be such as to not interfere with the synergistic effect attributable to the presence of the salicylate. Therefore, most preferably such other detergents are not employed.

If such additional detergents are present, they can include alkali and alkaline earth metal phenates, sulfonates, carboxylates, phosphonates and mixtures thereof. These supplemental detergents can have total base number (TBN) ranging from neutral to highly overbased, i.e. TBN of 0 to over 500, preferably 2 to 400, more preferably 5 to 300, and they can be present either individually or in combination with each other in an amount in the range of from 0 to 10 wt %, preferably 0.5 to 5 wt % (active ingredient) based on the total weight of the formulated lubricating oil. As previously stated, however, it is preferred that such other detergent not be present in the formulation.

Such additional other detergents include by way of example and not limitation calcium phenates, calcium sulfonates, magnesium phenates, magnesium sulfonates and other related components (including borated detergents).

Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the alkenylsuccinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary patents describing such dispersants are U.S. Pat. Nos. 3,172,892; 3,219,666; 3,316,177 and 4,234,435. Other types of dispersants are described in U.S. Pat. Nos. 3,036,003; and 5,705,458.

Hydrocarbyl-substituted succinic acid compounds are popular dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between alkenyl succinic anhydrides and amines. Molar ratios can vary depending on the amine or polyamine. For example, the molar ratio of alkenyl succinic anhydride to TEPA can vary from about 1:1 to about 5:1.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from about 0.1 to about 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from 800 to 2,500.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N—(Z—NH—)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Preferred dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of about 0.1 to 20 wt %, preferably about 0.1 to 8 wt %, more preferably about 1 to 6 wt % (on an as-received basis) based on the weight of the total lubricant.

Pour Point Depressants

Conventional pour point depressants (also known as lube oil flow improvers) may also be present. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of about 0.0 to 0.5 wt %, preferably about 0 to 0.3 wt %, more preferably about 0.001 to 0.1 wt % on an as-received basis.

Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles thiadiazoles and mixtures thereof. Such additives may be used in an amount of about 0.01 to 5 wt %, preferably about 0.01 to 1.5 wt %, more preferably about 0.01 to 0.2 wt %, still more preferably about 0.01 to 0.1 wt % (on an as-received basis) based on the total weight of the lubricating oil composition.

Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of about 0.01 to 3 wt %, preferably about 0.01 to 2 wt % on an as-received basis.

Anti-Foam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent, preferably 0.001 to about 0.5 wt %, more preferably about 0.001 to about 0.2 wt %, still more preferably about 0.0001 to 0.15 wt % (on an as-received basis) based on the total weight of the lubricating oil composition.

Inhibitors and Antirust Additives

Anti-rust additives (or corrosion inhibitors) are additives that protect lubricated metal surfaces against chemical attack by water or other contaminants. One type of anti-rust additive is a polar compound that wets the metal surface preferentially, protecting it with a film of oil. Another type of anti-rust additive absorbs water by incorporating it in a water-in-oil emulsion so that only the oil touches the surface. Yet another type of anti-rust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5 wt %, preferably about 0.01 to 1.5 wt % on an as-received basis.

In addition to the ZDDP anti-wear additives which are essential components of the present disclosure, other anti-wear additives can be present, including zinc dithiocarbamates, molybdenum dialkyldithiophosphates, molybdenum dithiocarbamates, other organo molybdenum-nitrogen complexes, sulfurized olefins, etc.

The term "organo molybdenum-nitrogen complexes" embraces the organo molybdenum-nitrogen complexes described in U.S. Pat. No. 4,889,647. The complexes are reaction products of a fatty oil, dithanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 cm$^{-1}$ and an amide carbonyl band at 1620 cm$^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used in the present disclosure are tri-nuclear molybdenum-sulfur compounds described in EP 1 040 115 and WO 99/31113 and the molybdenum complexes described in U.S. Pat. No. 4,978,464.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

Example 1

Synthesis of 1-(2-hexyldecyloxy)-4-methylbenzene using copper catalyzed coupling of 1-iodo-4-methylbenzene with 2-hexyldecane-1-ol

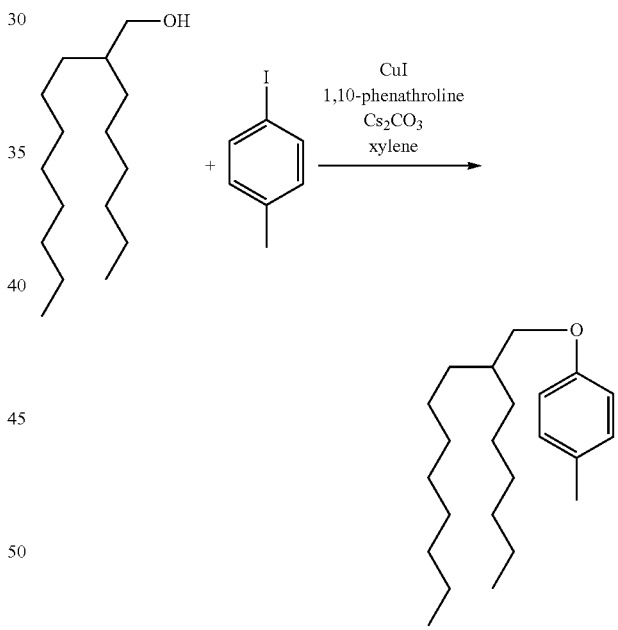

Charged 1-iodotoulene (10 grams, 45.865 mmol, MW: 218.03), 2-hexyldecan-1-ol (13.3 grams, 54.858 mmol, MW: 242.44), cesium carbonate, (31.94 grams, 66.789 mmol, MW: 328.5), 1,10-phenathroline (1.65 grams, 91.60 mmol, MW: 180.21), copper (I) iodide (0.894 grams, 4.58 mmol, MW: 195.01) and 70 milliliters dry xylene in 350 milliliter three necked round bottom flask. The reaction mixture was heated with stirring at 140° C. for 24 hours under nitrogen. The resulting suspension was cooled to room temperature and filtered through celite and alumina. The low boiling (xylene) component was removed by rotary evaporator and high boiling component by air bath oven at 200° C. under high vacuum for 1 hour. The residue was purified by flask chromatography on silica gel with hexane. The final colorless product yielded 7.2 grams (50%). The product $^{13}$C NMR analysis suggests the formation of alkylarylether product. $^{13}$C NMR (CDCl$_3$): 157.54, 129.84, 129.51, 141.44, 71.01, 38.06, 31.97, 31.93, 31.45, 30.11, 28.77, 29.66, 29.40, 26.91, 26.88, 22.74, 20.48, 14.16.

Example 2

Synthesis of 4-(2-hexyldecyloxy)-1,2-dimethylbenzene

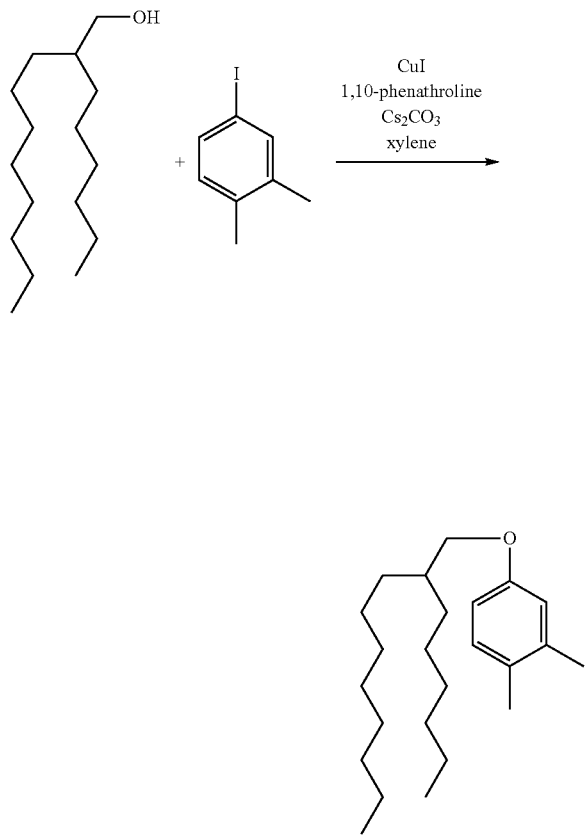

Charged 1-iodo-2,4-dimethylbenzene (10 grams, 43.09 mmol, MW: 232.06), 2-hexyldecan-1-ol (12.54 grams, 51.71 mmol, MW: 242.44), cesium carbonate, (21.23 grams, 64.62 mmol, MW: 328.5), 1,10-phenathroline (1.55 grams, 8.601 mmol, MW: 180.21), copper (1) iodide (0.840 grams, 4.307 mmol, MW: 195.01) and 100 ml dry xylene in 350 milliliter three necked round bottom flask. The reaction mixture was heated with stirring at 140° C. for 24 hours under nitrogen. The resulting suspension was cooled to room temperature and filtered through celite and alumina. The low boiling (xylene) component removed by rotary evaporator and high boiling component by air bath oven at 200° C. under high vacuum for 1 hour. The residue was purified by flask chromatography on silica gel with hexane. The final colorless product yielded 7.0 grams (47%). The product $^{13}$C NMR analysis suggests the formation of alkylarylther product. $^{13}$C NMR (CDCl$_3$): 158.01, 137.65, 130.27, 128.24, 116.28, 111.19, 70.99, 37.91, 32.12, 31.61, 30.18, 29.85, 29.47, 26.97, 22.90, 20.10, 18.83, 14.19.

Example 3

Synthesis of 2-(2-ethylhexyloxy)naphthalene via coupling of 2-naphthol with 2-ethylhexylbromide

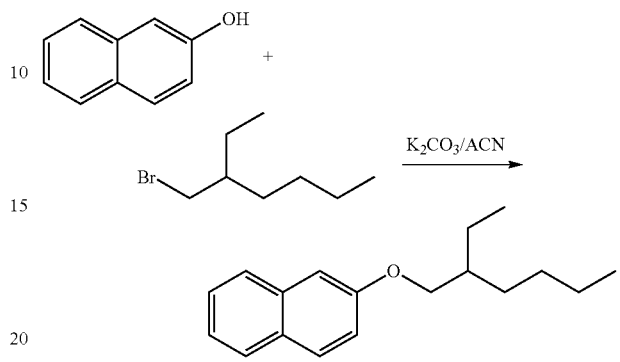

Charged 2-naphthol (5 g, 34.68 mmol, MW: 144.17), potassium carbonate (7.18 grams, 52.02 mmol, MW: 138.21), benzyl tributylammonium bromide (1.24 grams, 3.468 mmol, MW: 356.38) and 75 ml acetonitrile (ANC) in 350 milliliter three necked round bottom flask under N$_2$ atmosphere. Added slowly 2-ethylhexylbromide (10.05 grams, 52.02 mmol, MW: 193.12) at room temperature. After addition, the reaction mixture was stir for 18 hours at 70° C. Stopped the reaction and removed the inorganic salts (KBr and excess K$_2$CO$_3$). Evaporated the ACN and extracted the product with (IX 75 milliliters) hexane. The organic extract was washed with (1×50 milliliters) 2N saturated KOH solution and water (1×75 milliliters) until, the aqueous layer pH ~7. The product was dried and filtered. The low boiling (hexane) component was removed by rotary evaporator and high boiling component (2-ethylhexylbromide) by air bath oven at 180° C. under high vacuum for 1 hour. The final crude was purified by flash chromatography with hexane. The product was determined by $^1$HNMR. Yields: 6.60 g (~74%). $^1$H NMR (CDCl$_3$): δ 7.60-7.11 (m, 7H, naphthyl-), 3.93 (d, 2H, —OCH$_2$—), 1.78 (m, 1H, —CH$_2$—) 1.40-1.33 (m, 8H, —CH$_2$—), 0.94 (t, 6H, —CH$_3$).

Example 4

Synthesis of 3-heptyloxy-26-diphenylmethane

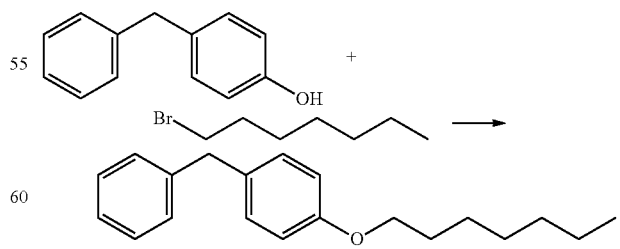

A 2-neck round-bottomed flask was charged with acetonitrile (400 milliliters) and potassium carbonate (150 grams, 1.085 moles). The mixture was stirred and 4-benzylphenol (70 grams, 380 millimoles) was added. The mixture was heated to reflux under nitrogen for 3 hours, then allowed to cool down, 1-bromoheptane (110 grams, 614.2 millimoles) and additional acetonitrile (100 milliliters) were added. The mixture was reheated to reflux and maintained for 16 hours. After the reaction mixture was cooled down, it was filtered and the precipitate was washed with methylene chloride. The combined filtrate was concentrated and diluted with methylene chloride. The solution was washed with potassium hydroxide aqueous solution (3 moles/liter), hydrogen chloride solution (3 moles/liter) twice and distilled water sequentially. The organic phase was dried over magnesium sulfate, and evaporated under vacuum to remove the solvent. The crude product was purified by vacuum distillation using a Kugelrohr apparatus. The final product was determined by $^1$H NMR. $^{13}$C NMR and GC. Yields: 99.4 grams (93%). $^1$H NMR (CDCl$_3$): δ 7.24-6.78 (9H, Ph), 3.88 (s and t, 4H, PhCH$_2$Ph- and —OCH$_2$—), 1.75 (m, 2H, —OCH$_2$CH$_2$—), 1.44-1.30 (m, 8H, —OCH$_2$CH$_2$(CH$_2$)$_4$CH$_3$), 0.88 (t, 3H, —CH$_3$). $^{13}$C NMR (CDCl$_3$): 157.5, 141.6, 132.9, 129.8, 128.8, 128.3, 125.9, 114.4 (Ph), 67.9 (—OCH$_2$—), 41.0 (PhCH$_2$Ph-), 31.8 (—CH$_2$CH$_2$CH$_3$), 29.3, 29.1 (—OCH$_2$CH$_2$CH$_2$CH$_2$CH$_2$CH$_3$), 26.0 (—OCH$_2$CH$_2$CH$_2$—), 22.6 (—CH$_2$CH$_3$), 14.1 (—CH$_3$).

Example 5

Synthesis of 3-nonyloxy-2,6-diphenylmethane

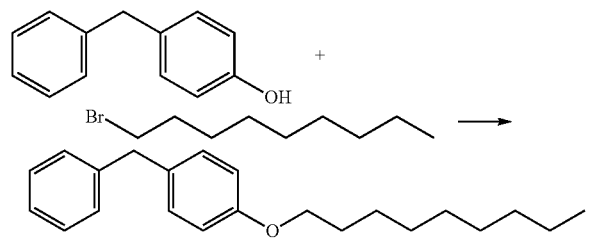

A 2-neck round-bottomed flask was charged with acetonitrile (68 milliliters) and potassium carbonate (22 grams). The mixture was stirred and 4-benzylphenol (10 grams) was added. The mixture was heated to reflux under nitrogen for 3 hours, then allowed to cool down. 1-bromononane (18 grams) and additional acetonitrile (34 milliliters) were added. The mixture was reheated to reflux and maintained for 16 hours. After the reaction mixture was cooled down, it was filtered and the precipitate was washed with methylene chloride. The combined filtrate was concentrated and diluted with methylene chloride. The solution was washed with potassium hydroxide aqueous solution (3 moles/liter), hydrogen chloride solution (3 moles/liter) twice and distilled water sequentially. The organic phase was dried over magnesium sulfate, and evaporated under vacuum to remove the solvent. The crude product was purified by vacuum distillation using a Kugelrohr apparatus. The final product was determined by $^1$H NMR, $^{13}$C NMR and GC. Yields: 15.7 grams (93%). $^1$H NMR (CDCl$_3$): δ 7.26-6.80 (9H, Ph), 3.91 (s and t, 4H, PhCH$_2$Ph- and —OCH$_2$—), 1.75 (m, 2H, —OCH$_2$CH$_2$—), 1.41-1.27 (m, 12H, —OCH$_2$CH$_2$(CH$_2$)$_6$CH$_3$), 0.88 (t, 3H, —CH$_3$). $^{13}$C NMR (CDCl$_3$): 157.5, 141.6, 133.0, 129.8, 128.8, 128.4, 125.9, 114.5 (Ph), 68.0 (—OCH$_2$—), 41.0 (PhCH$_2$Ph-), 31.9 (—CH$_2$CH$_2$CH$_3$), 29.5-29.3 (—OCH$_2$CH$_2$CH$_2$(CH$_2$)$_3$CH$_2$CH$_2$CH$_3$), 26.1 (—OCH$_2$CH$_2$CH$_2$—), 22.7 (—CH$_2$CH$_3$), 14.1 (—CH$_3$).

Example 6

Synthesis of Blend Mixture

A blend mixture of the product of Example 4 and the product of Example 5 was prepared (50:50 by weight).

Example 7

Synthesis of 3-(2-ethylhexyloxy)-2,6-diphenylmethane

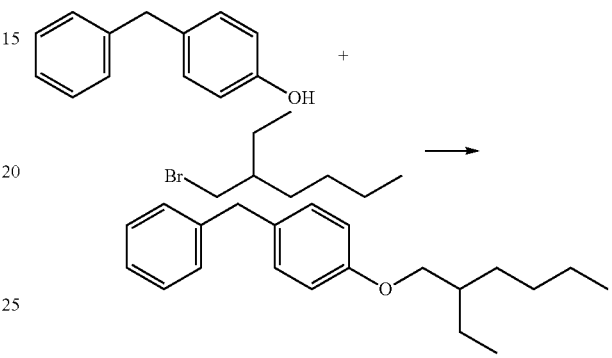

A 2-neck round-bottomed flask was charged with acetonitrile (500 milliliters) and potassium carbonate (130 grams, 940.7 millimoles). The mixture was stirred and 4-benzylphenol (60 grams, 325.7 millimoles) was added. The mixture was heated to reflux under nitrogen for 3 hours, then allowed to cool down. 2-Ethylhexyl bromide (100 grams, 517.8 millimoles) was added. The mixture was reheated to reflux and maintained for 16 hours. After the reaction mixture was cooled down, it was filtered and the precipitate was washed with methylene chloride. The combined filtrate was concentrated and diluted with methylene chloride. The solution was washed with potassium hydroxide aqueous solution (3 moles/liter), hydrogen chloride solution (3 moles/liter) twice and distilled water sequentially. The organic phase was dried over magnesium sulfate, and evaporated under vacuum to remove the solvent. The crude product was purified by vacuum distillation using a Kugelrohr apparatus. The final product was determined by $^1$H NMR and GC. Yields: 57.3 (60%). $^1$H NMR (CDCl$_3$): δ 7.27-6.81 (m, 9H, Ph), 3.89 (s, 2H, PhCH$_2$Ph-), 3.79 (d, 2H, —OCH$_2$—) 1.69 (m, 1H, —OCH$_2$CH(Et)-), 1.49-1.28 (m, 8H, —OCH$_2$CH(CH$_2$CH$_3$)CH$_2$CH$_2$CH$_2$CH$_3$), 0.91 (t, 6H, —OCH$_2$CH(CH$_2$CH$_3$)CH$_2$CH$_2$CH$_2$CH$_3$).

Example 8

Synthesis of 1-(2-butyloctyloxy)naphthalene

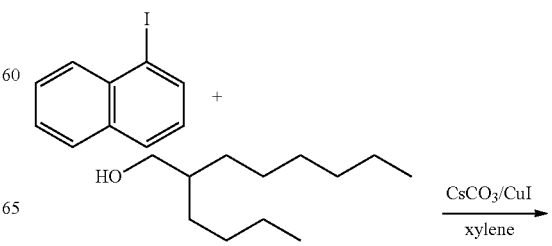

-continued

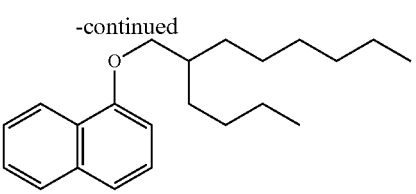

Charged 1-iodonapthalene (5 grams, 19.679 mmol, MW: 254.07), 2-butyl-1-octanol (7.34 grams, 39.416 mmol, MW: 186.28), cesium carbonate, (9.7 grams, 29.528 mmol, MW: 328.5), 1,10-phenanthroline (0.709 grams, 3.94 mmol, MW: 180.21), copper (I) iodide (0.384 grams, 1.97 mmol, MW: 195.01) and 50 milliliters of dry xylene in 350 milliliter three necked round bottom flask. The reaction mixture was heated with stirring at 140° C. for 24 hours under nitrogen. The resulting suspension was cooled to room temperature and filtered through celite. The filtrate was concentrated at 180° C. under high vacuum. The residue was purified by flask chromatography on silica gel with hexane. The final pale yellow product was yielded 3.76 grams (61%). The $^{13}$C NMR analysis of the product suggests the formation of desired naphthyl ether fluid. $^{13}$C NMR (CDCl$_3$): 154.03, 133.47, 126.38, 125.21, 124.89, 124.77, 123.99, 121.10, 118.79, 103.29, 69.66, 37.05, 30.86, 30.33, 28.67, 28.14, 25.89, 22.07, 21.66, 13.08.

Example 9

Synthesis of 2-(3,7-dimethyloctyloxy)naphthalene

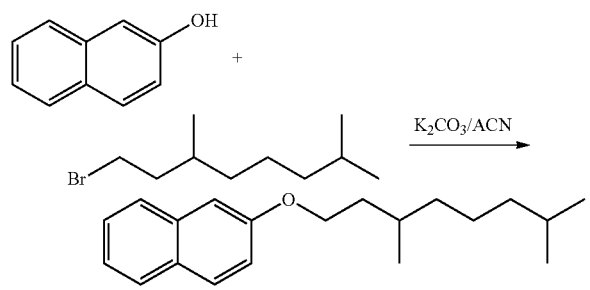

Charged 2-napthaol (5 grams, 34.68 mmol, MW: 144.17), potassium carbonate (6.46 grams, 46.80 mmol, MW: 138.21), benzyl tributylammonium bromide (1.24 grams, 3.468 mmol, MW: 356.38) and 75 milliliters of acetonitrile (ANC) in 350 milliliter three necked round bottom flask under N$_2$ atmosphere. Added slowly 1-bromo-3,7-dimethyloctane (10.36 grams, 46.80 mmol, MW: 193.12) at room temperature. After addition, the reaction mixture was stir for 12 hours at 75° C. Stopped the reaction and remove the inorganic salts (KBr and excess K$_2$CO$_3$). Evaporated the solvent ACN and extracted the product with (1×75 milliliters) hexane. The organic extract was washed with (1×50 milliliters) 2N saturated KOH solution and water (1×75 milliliters) until, the aqueous layer pH ~7. Dry and filter the product. The low boiling (hexane) component removed by rotary evaporator and high boiling component (1-bromo-3,7-dimethyloctane) by air bath oven at 180° C. under high vacuum for 1 hour. The final crude was purified by flash chromatography with hexane. The $^1$H NMR analysis of the product suggests the formation of desired naphthyl fluid. Yields: 7.50 grams (~76%). $^1$H NMR (CDCl$_3$): δ 7.71-7.13 (m, 7H, naphthyl-), 4.09 (d, 2H, —OCH$_2$—), 1.88 (m, 1H, —CH$_2$—) 1.37-1.37 (m, 6H, —CH$_2$—), 0.98-088 (t, 9H, —CH$_3$).

Example 10

Synthesis of 1-(2-ethylhexyloxy)naphthalene

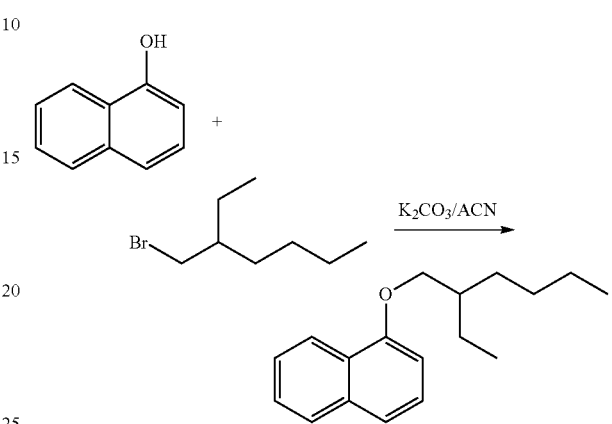

Charged 1-napthaol (5 grams, 34.68 mmol, MW: 144.17), potassium carbonate (7.18 grams, 52.02 mmol, MW: 138.21), benzyl tributylammonium bromide (1.24 grams, 3.468 mmol, MW: 356.38) and 75 milliliters acetonitrile (ANC) in 350 milliliter three necked round bottom flask under N$_2$ atmosphere. Added slowly 2-ethylhexylbromide (10.05 grams, 52.02 mmol, MW: 193.12) at room temperature. After addition, the reaction mixture was stirred for 18 hours at 70° C. Stopped the reaction and remove the inorganic salts (KBr and excess K2CO3). Evaporated the ACN and extracted the product with (1×75 milliliters) hexane. The organic extract was washed with (1×50 milliliters) 2N saturated KOH solution and water (1×75 milliliters) until, the aqueous layer pH ~7. Dry and filter the product. The low boiling (hexane) component removed by rota vapory and high boiling component (2-ethylhexylbromide) by air bath oven at 180° C. under high vacuum for 1 hour. The final crude was purified by flash chromatography with hexane. The $^1$H NMR analysis of the product suggests the formation of desired naphthyl fluid. Yields: 6.5 grams (~73%). $^1$H NMR (CDCl$_3$): δ 8.26-6.79 (m, 7H, naphthyl-), 4.01 (d, 2H, —OCH$_2$—), 1.86 (m, 1H, —CH$_2$—) 1.57-1.34 (m, 8H, —CH$_2$—), 0.96 (t, 6H, —CH$_3$), 0.90 (t, 6H, —CH$_3$).

Example 11

Lube Properties

The lube properties of the products of Examples 1-10 were evaluated and the data are shown in FIG. 1 and FIG. 2. The kinematic viscosity (Kv) of the liquid product was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The product volatility was measured using thermogravimetric analysis (TGA) based Noack. Noack volatility was determined by ASTM D-5800. These fluids were evaluated as Group V base stocks and the results are shown in FIG. 1.

By changing the glycol ether portion, molecules with varying polarity can be synthesized. These molecules can be used as low viscosity base stocks or can be used as cobase stocks along with mPAO, PAO, Group I-III+, GTL. This fuel economy enabling base stock provide opportunity for step-out lubricants with distinguishable and marketable features. Besides base stocks there molecules can also be used as a non-phthalate, non-ester but ether based PVC plasticizers.

The fluids have improved viscosity-volatility characteristics compared to hydrocarbons fluids such as PAO4, mPAO3.4, PAO2, and mPAO2, as shown in FIG. 2.

Example 12

Lube Properties

The fluid of Example 6 shows desirable high temperature high shear (HTHS) viscosity, volatility and TEOST (thermo-oxidation engine oil determination of high temperature piston deposits) results for low-viscosity engine oils formulated with base stocks of this disclosure. The HTHS test was conducted in accordance with ASTM D5481. The product volatility was measured using thermogravimetric analysis (TGA) based Noack. Noack volatility was determined by ASTM D-5800. The TEOST test was conducted in accordance with ASTM D7097-09.

The fluid of Example 6 was formulated with an additive package composed of commonly used additive components. The formulation consisted of 82.3% by weight of the base stock together with 17.7% by weight of the additive package. It has been found that Example 6 base stock exhibits high solvency for the typical additive components (e.g., antiwear additives, friction modifiers, dispersants, detergents, antioxidants, viscosity modifiers, pour point depressants, antifoaming agent, etc.) employed in the formulation of lubricants. A formulated oil using the base stock of Example 6 has an HTHS of 1.66, suggesting one can formulate a very low viscosity engine oil, i.e. "0W-4" or lower. By comparison, PAO4 has an HTHS of 1.97 cp suggesting that the lowest viscosity oil that can be formulated with PAO 4 would be 0W-08.

Figure 3:
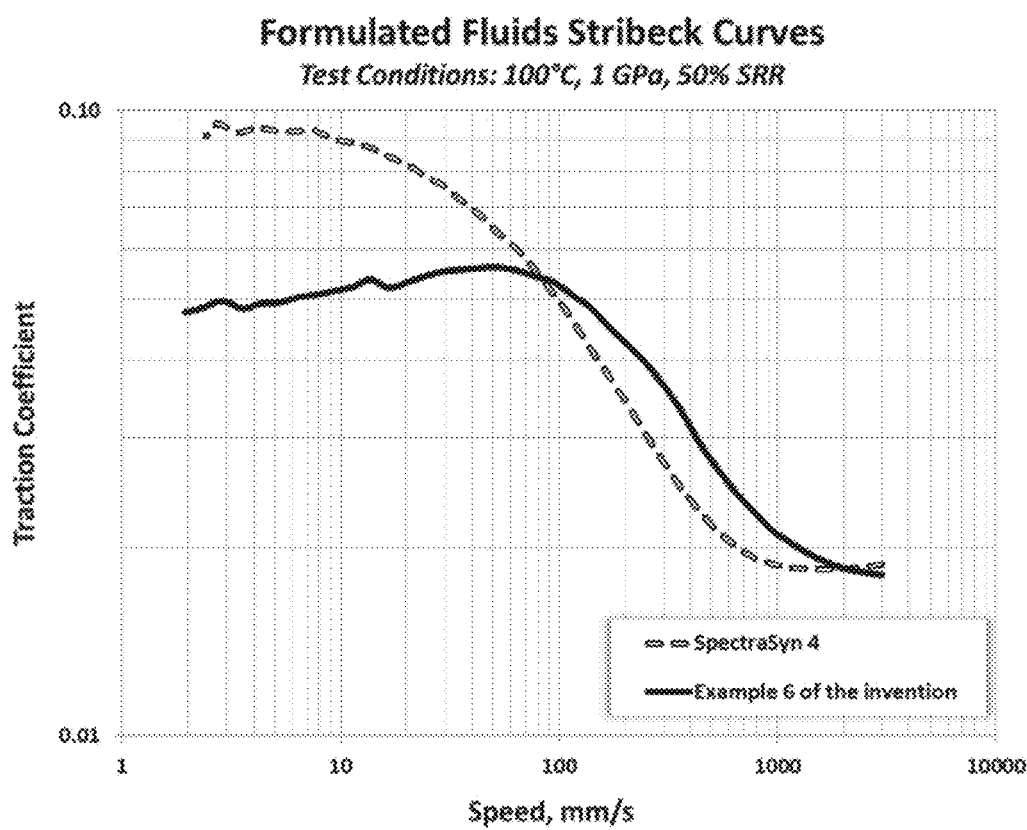
FIG. 3 shows MTM Stribeck curves from the Spectrasyn4 formulation and the Example 6 formulation finished oil performance in MTM (mini-traction machine) Stribeck test at 100° C. (log and mean speed) in accordance with Example 12.

FIG. 3 shows MTM Stribeck curves from the Spectrasyn4 formulation and the Example 6 formulation finished oil performance in MTM (mini-traction machine) Stribeck test at 100° C. and 1.00 GPa (log and mean speed). MTM friction average was measured by WI307SF-9.

The product of Example 6 also showed significantly lower traction coefficient (in the lower speed boundary lubrication area of the Stribeck curve) than products formulated with SpectraSyn4 (FIG. 3). The combination of low viscosity, high stability and low traction coefficient makes Example 6 a desired base stock for engine oil with improved engine durability and fuel efficiency.

PCT AND EP CLAUSES

1. A composition comprising one or more compounds represented by the formula

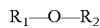

wherein $R_1$ is a substituted or unsubstituted aryl or polyaryl group having from 4 to 40 carbon atoms, and $R_2$ is a substituted or unsubstituted, linear or branched, alkyl group having from 4 to 40 carbon atoms; wherein said composition has a viscosity ($Kv_{100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

2. The composition of clause 1 wherein $R_1$ is substituted or unsubstituted phenyl, benzyl, naphthyl, or diphenyl, and $R_2$ is substituted or unsubstituted, linear or branched, alkyl ($C_4$-$C_{40}$).

3. The composition of clauses 1 and 2 which is selected from one or more compounds represented by the formulae

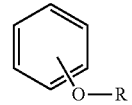

wherein R is a substituted or unsubstituted, linear or branched, alkyl group having from 4 to 40 carbon atoms:

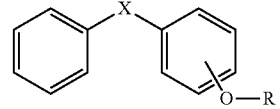

wherein R is a substituted or unsubstituted, linear or branched, alkyl group having from 4 to 40 carbon atoms, and X is $CH_2$, O, NR' or S, wherein R' is hydrogen or an alkyl group having from 1 to 4 carbon atoms; and

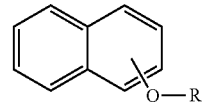

wherein R is a substituted or unsubstituted, linear or branched, alkyl group having from 4 to 40 carbon atoms.

4. The composition of clauses 1-3 which is selected from 1-(2-hexyldecyloxy)-4-methylbenzene, 4-(2-hexyldecyloxy)-1,2-dimethylbenzene, 2-(2-ethylhexyloxy)naphthalene, 3-heptyloxy-2,6-diphenylmethane, 3-nonyloxy-2,6-diphenylmethane, 3-(2-ethylhexyloxy)-2,6-diphenylmethane, 1-(2-butyloctyloxy)naphthalene, 2-(3,7-dimethyloctyloxy) naphthalene, and 2-(2-ethylhexyloxy)naphthalene.

5. A composition comprising one or more alkyl substituted aryl ethers represented by the formula

wherein $R_1$ is a substituted or unsubstituted aryl or polyaryl group having from 4 to 40 carbon atoms, and $R_2$ is a substituted or unsubstituted, linear or branched, alkyl group having from 4 to 40 carbon atoms; wherein said composition has a viscosity ($Kv_{100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800; wherein said one or more alkyl substituted aryl ethers are produced by a process comprising reacting a substituted or unsubstituted aryl alcohol with a substituted or unsubstituted alkyl halide, optionally in the presence of a catalyst, under reaction conditions sufficient to produce said one or more alkyl substituted aryl ethers.

6. A composition comprising one or more alkyl substituted aryl ethers represented by the formula

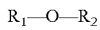

wherein $R_1$ is a substituted or unsubstituted aryl or polyaryl group having from 4 to 40 carbon atoms, and $R_2$ is a substituted or unsubstituted, linear or branched, alkyl group having from 4 to 40 carbon atoms; wherein said composition has a viscosity ($Kv_{100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800; wherein said one or more alkyl substituted aryl ethers are produced by a process comprising reacting a substituted or unsubstituted aryl halide with a substituted or unsubstituted alkyl alcohol, optionally in the presence of a catalyst, under reaction conditions sufficient to produce said one or more alkyl substituted aryl ethers.

7. A lubricating oil base stock comprising one or more compounds represented by the formula

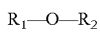

wherein $R_1$ is a substituted or unsubstituted aryl or polyaryl group having from 4 to 40 carbon atoms, and $R_2$ is a substituted or unsubstituted, linear or branched, alkyl group having from 4 to 40 carbon atoms; wherein said lubricating oil base stock has a viscosity ($Kv_{100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

8. The lubricating oil base stock of clause 7 wherein $R_1$ is substituted or unsubstituted phenyl, benzyl, naphthyl, or diphenyl, and $R_2$ is substituted or unsubstituted alkyl ($C_4$-$C_{40}$).

9. The lubricating oil base stock of clauses 7 and 8 which is selected from one or more compounds represented by the formulae

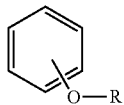

wherein R is a substituted or unsubstituted, linear or branched, alkyl group having from 4 to 40 carbon atoms;

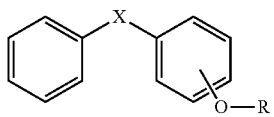

wherein R is a substituted or unsubstituted, linear or branched, alkyl group having from 4 to 40 carbon atoms, and X is $CH_2$, O, NR' or S, wherein R' is hydrogen or an alkyl group having from 1 to 4 carbon atoms; and

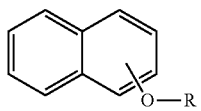

wherein R is a substituted or unsubstituted, linear or branched, alkyl group having from 4 to 40 carbon atoms.

10. The lubricating oil base stock of clauses 7-9 which is selected from 1-(2-hexyldecyloxy)-4-methylbenzene, 4-(2-hexyldecyloxy)-1, 2-dimethylbenzene, 2-(2-ethylhexyloxy) naphthalene, 3-heptyloxy-2, 6-diphenylmethane, 3-nonyloxy-2,6-diphenylmethane, 3-(2-ethylhexyloxy)-2, 6-diphenylmethane, 1-(2-butyloctyloxy)naphthalene, 2-(3, 7-dimethyloctyloxy)naphthalene, and 2-(2-ethylhexyloxy) naphthalene.

11. A lubricating oil comprising a lubricating oil base stock as a major component, and an alkyl substituted aryl ether cobase stock as a minor component; wherein said alkyl substituted aryl ether cobase stock comprises one or more compounds represented by the formula

wherein $R_1$ is a substituted or unsubstituted aryl or polyaryl group having from 4 to 40 carbon atoms, and $R_2$ is a substituted or unsubstituted, linear or branched, alkyl group having from 4 to 40 carbon atoms; wherein said lubricating oil has a viscosity ($Kv_{100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

12. The lubricating oil of clause 11 wherein, in the alkyl substituted aryl ether cobase stock, $R_1$ is substituted or unsubstituted phenyl, benzyl, naphthyl, or diphenyl, and $R_2$ is substituted or unsubstituted alkyl ($C_4$-$C_{40}$).

13. The lubricating oil of clauses 11 and 12 wherein the alkyl substituted aryl ether cobase stock is selected from one or more compounds represented by the formulae

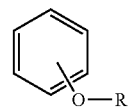

wherein R is a substituted or unsubstituted, linear or branched, alkyl group having from 4 to 40 carbon atoms:

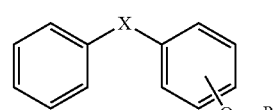

wherein R is a substituted or unsubstituted, linear or branched, alkyl group having from 4 to 40 carbon atoms, and X is $CH_2$, O, NR' or S, wherein R' is hydrogen or an alkyl group having from 1 to 4 carbon atoms; and

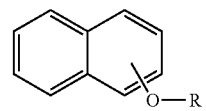

wherein R is a substituted or unsubstituted, linear or branched, alkyl group having from 4 to 40 carbon atoms.

14. The lubricating oil of clauses 11-13 wherein the alkyl substituted aryl ether cobase stock is selected from 1-(2-hexyldecyloxy)-4-methylbenzene, 4-(2-hexyldecyloxy)-1, 2-dimethylbenzene, 2-(2-ethylhexyloxy)naphthalene, 3-heptyloxy-2,6-diphenylmethane, 3-nonyloxy-2, 6-diphenylmethane, 3-(2-ethylhexyloxy)-2,6-diphenylmethane, 1-(2-butyloctyloxy)naphthalene, 2-(3,7-dimethyloctyloxy)naphthalene, and 2-(2-ethylhexyloxy)naphthalene.

15. A method of reducing the boundary friction and dispersancy of polar additives of a lubricating oil by using as the lubricating oil a formulated oil comprising a lubricating oil base stock as a major component, and alkyl substituted aryl ether cobase stock as a minor component; wherein said alkyl substituted aryl ether cobase stock comprises one or more compounds represented by the formula

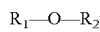

wherein $R_1$ is a substituted or unsubstituted aryl or polyaryl group having from 4 to 40 carbon atoms, and $R_2$ is a substituted or unsubstituted, linear or branched, alkyl group having from 4 to 40 carbon atoms; wherein said lubricating oil has a viscosity ($Kv_{100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

The invention claimed is:

1. A composition comprising one or more compounds represented by the formula

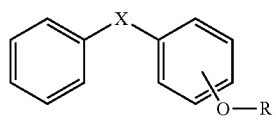

wherein R is a substituted or unsubstituted, linear or branched, alkyl group having from 4 to 40 carbon atoms, and X is O, NR' or S, wherein R' is hydrogen or an alkyl group having from 1 to 4 carbon atoms; wherein said composition has a viscosity ($K_{V100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

2. The composition of claim 1 which has a viscosity ($K_{V100}$) from 1 to 8 cSt at 100° C. as determined by ASTM D-445, a viscosity index (VI) from 25 to 125 as determined by ASTM D-2270, and a Noack volatility of no greater than 25 percent as determined by ASTM D-5800.

3. A composition comprising one or more alkyl substituted aryl ethers represented by the formula

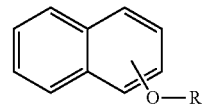

wherein R is a substituted or unsubstituted, linear or branched, alkyl group having from 4 to 40 carbon atoms, and X is O, NR' or S, wherein R' is hydrogen or an alkyl group having from 1 to 4 carbon atoms; wherein said composition has a viscosity ($K_{V100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800;

wherein said one or more alkyl substituted aryl ethers are produced by a process comprising reacting a substituted or unsubstituted aryl alcohol with a substituted or unsubstituted alkyl halide, optionally in the presence of a catalyst, under reaction conditions sufficient to produce said one or more alkyl substituted aryl ethers.

4. A composition comprising one or more alkyl substituted aryl ethers represented by the formula

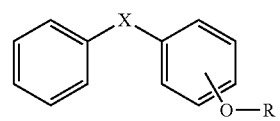

wherein R is a substituted or unsubstituted, linear or branched, alkyl group having from 4 to 40 carbon atoms, and X is O, NR' or S, wherein R' is hydrogen or an alkyl group having from 1 to 4 carbon atoms; wherein said composition has a viscosity ($K_{V100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800;

wherein said one or more alkyl substituted aryl ethers are produced by a process comprising reacting a substituted or unsubstituted aryl halide with a substituted or unsubstituted alkyl alcohol, optionally in the presence of a catalyst, under reaction conditions sufficient to produce said one or more alkyl substituted aryl ethers.

5. A lubricating oil base stock comprising one or more compounds represented by the formula

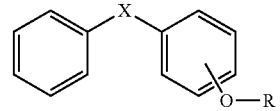

wherein R is a substituted or unsubstituted, linear or branched, alkyl group having from 4 to 40 carbon atoms, and X is O, NR' or S, wherein R' is hydrogen or an alkyl group having from 1 to 4 carbon atoms; wherein said lubricating oil base stock has a viscosity ($K_{V100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

6. The lubricating oil base stock of claim 5 which has a viscosity ($K_{V100}$) from 1 to 8 cSt at 100° C. as determined by ASTM D-445, a viscosity index (VI) from 25 to 125 as determined by ASTM D-2270, and a Noack volatility of no greater than 25 percent as determined by ASTM D-5800.

7. A lubricating oil comprising a lubricating oil base stock as a major component, and an alkyl substituted aryl ether cobase stock as a minor component; wherein said alkyl substituted aryl ether cobase stock comprises one or more compounds represented by the formula

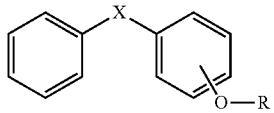

wherein R is a substituted or unsubstituted, linear or branched, alkyl group having from 4 to 40 carbon atoms, and X is O, NR' or S, wherein R' is hydrogen or an alkyl group having from 1 to 4 carbon atoms; wherein said lubricating oil has a viscosity ($K_{V100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

8. The lubricating oil of claim 7 wherein the lubricating oil base stock comprises a Group I, II, III, IV or V base oil stock.

9. The lubricating oil of claim 7 wherein the lubricating oil base stock comprises a polyalphaolefin (PAO) or gas-to-liquid (GTL) oil base stock.

10. The lubricating oil of claim 7 wherein the lubricating oil base stock is present in an amount from 50 weight percent to 99 weight percent, and the alkyl substituted aryl ether cobase stock is present in an amount from 1 weight percent to 30 weight percent, based on the total weight of the lubricating oil.

11. The lubricating oil of claim 7 which has a viscosity ($K_{V100}$) from 1 to 8 cSt at 100° C. as determined by ASTM D-445, a viscosity index (VI) from 25 to 125 as determined by ASTM D-2270, and a Noack volatility of no greater than 25 percent as determined by ASTM D-5800.

12. A method of reducing boundary friction and improving dispersancy of polar additives of a lubricating oil by using as the lubricating oil a formulated oil comprising a lubricating oil base stock as a major component, and alkyl substituted aryl ether cobase stock as a minor component; wherein said alkyl substituted aryl ether cobase stock comprises one or more compounds represented by the formula

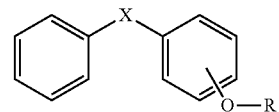

wherein R is a substituted or unsubstituted, linear or branched, alkyl group having from 4 to 40 carbon atoms, and X is O, NR' or S, wherein R' is hydrogen or an alkyl group having from 1 to 4 carbon atoms; wherein said lubricating oil has a viscosity ($K_{V100}$) from 1 to 10 cSt at 100° C. as determined by ASTM D-445, a viscosity index (VI) from −100 to 300 as determined by ASTM D-2270, and a Noack volatility of no greater than 50 percent as determined by ASTM D-5800.

13. The method of claim 12 wherein the alkyl substituted aryl ether cobase stock has a viscosity ($K_{V100}$) from 1 to 8 cSt at 100° C. as determined by ASTM D-445, a viscosity index (VI) from 25 to 125 as determined by ASTM D-2270, and a Noack volatility of no greater than 25 percent as determined by ASTM D-5800.

* * * * *